US 6,689,080 B2

(12) United States Patent
Castillo (10) Patent No.: US 6,689,080 B2
(45) Date of Patent: Feb. 10, 2004

(54) JOINT BRACE WITH LIMB-CONFORMING ARCUATELY ADJUSTABLE CUFFS

(75) Inventor: James D. Castillo, Los Alamos, CA (US)

(73) Assignee: Asterisk.Asterisk LLC, Foothill Ranch, CA (US)

( * ) Notice: Subject to any disclaimer, the term of this patent is extended or adjusted under 35 U.S.C. 154(b) by 0 days.

(21) Appl. No.: 10/067,565

(22) Filed: Feb. 4, 2002

(65) Prior Publication Data

US 2002/0107464 A1 Aug. 8, 2002

Related U.S. Application Data

(63) Continuation-in-part of application No. 09/578,125, filed on May 24, 2000, now Pat. No. 6,464,657.

(51) Int. Cl.$^7$ .................................................. A61F 5/00
(52) U.S. Cl. ................................ 602/26; 602/5; 602/16
(58) Field of Search .......................... 602/5, 16, 18–19, 602/20, 23, 26, 60–63; 128/878–882; 623/27, 39, 57, 59; 2/59–60; 70/16, 18; 119/816, 726, 769–770; 24/41.1, 42

(56) References Cited

U.S. PATENT DOCUMENTS

| | | | | |
|---|---|---|---|---|
| 1,081,148 A | * | 12/1913 | Quayle | ........................ 604/308 |
| 1,388,772 A | * | 8/1921 | Sheehan | ...................... 602/63 |
| 1,390,915 A | | 9/1921 | Loth | |
| 2,531,486 A | | 11/1950 | Weber | |
| 2,883,982 A | | 4/1959 | Rainey | |
| 3,030,634 A | | 4/1962 | Blair | |
| 3,099,448 A | | 7/1963 | Salvo | |
| 3,387,305 A | | 6/1968 | Shafer | |
| 3,669,105 A | | 6/1972 | Castiglia | |
| 3,779,654 A | | 12/1973 | Horne | |
| 3,785,372 A | | 1/1974 | Craig | |

(List continued on next page.)

FOREIGN PATENT DOCUMENTS

| | | |
|---|---|---|
| DE | 1491569 | 7/1969 |
| DE | 2432766 | 3/1975 |
| EP | 297766 | 4/1989 |
| WO | 8400533 | 11/1984 |

OTHER PUBLICATIONS

"Strength and Motor Task Performance as Effected by the Carbon Titanium Knee Brace in Normal Health Males", by T.K. Iglehart, 1985, Colorado State Univ. Dept. of Physical Education, Fort Collins, Colo. Springs, 1985, pp. 1–12.

Primary Examiner—Jerome W. Donnelly (57) ABSTRACT

An exteriorly positionable anatomical brace for stabilizing a uniting pivoting joint disposed between a first and second limb structure of a living being. The brace includes upper and lower frame members joined by a pivoting joint member, with each frame member having a respective cuff for encompassing a portion of each limb structure above and below the joint. Each cuff is an arcuate, tensionable, flexibly-bendable wall structure having integral therewith at least one elongate tensioner in arcuately related juxtaposition with the cuff such that bending the tensioner also bends the cuff. The tensioner includes an exteriorly accessible adjuster for incrementally moving the lateral end of the tensioner medially or laterally for tightening or loosening the cuff. Once set, the adjuster maintains the chosen arcuate configuration, thereby assuring a proper fit without repeated adjustment each time the brace is donned.

11 Claims, 11 Drawing Sheets

U.S. PATENT DOCUMENTS

| | | |
|---|---|---|
| 3,817,244 A | 6/1974 | Taylor |
| 3,900,898 A | 8/1975 | Ackerman |
| 3,902,482 A | 9/1975 | Taylor |
| 3,928,872 A | 12/1975 | Johnson |
| 3,958,569 A * | 5/1976 | Vosburgh ..................... 602/16 |
| 4,048,991 A * | 9/1977 | Marx .......................... 602/64 |
| 4,136,404 A | 1/1979 | Lange |
| 4,169,467 A | 10/1979 | Rabischong et al. |
| 4,237,708 A * | 12/1980 | Bremer, Jr. .................... 70/16 |
| 4,241,730 A | 12/1980 | Helfet |
| 4,271,831 A | 6/1981 | Deibert |
| 4,361,142 A | 11/1982 | Lewis et al. |
| 4,372,298 A | 2/1983 | Lerman |
| 4,381,768 A | 5/1983 | Erichsen et al. |
| D269,379 S | 6/1983 | Bledsoe |
| 4,407,276 A | 10/1983 | Bledsoe |
| 4,428,369 A | 1/1984 | Peckham et al. |
| 4,487,200 A | 12/1984 | Feanny et al. |
| 4,489,718 A | 12/1984 | Martin |
| 4,493,316 A | 1/1985 | Reed et al. |
| 4,494,534 A | 1/1985 | Hutson |
| 4,503,846 A | 3/1985 | Martin |
| 4,523,585 A | 6/1985 | Lamb et al. |
| 4,554,913 A | 11/1985 | Womack et al. |
| D284,702 S | 7/1986 | Castillo |
| 4,599,998 A | 7/1986 | Castillo |
| 4,603,690 A | 8/1986 | Skeen |
| 4,614,181 A | 9/1986 | Karlsson |
| 4,620,532 A | 11/1986 | Houswerth |
| 4,621,624 A | 11/1986 | Rayboy |
| 4,628,916 A | 12/1986 | Lerman et al. |
| 4,665,905 A | 5/1987 | Brown |
| 4,681,097 A | 7/1987 | Pansier |
| 4,697,583 A | 10/1987 | Mason et al. |
| 4,699,129 A | 10/1987 | Aaserude et al. |
| 4,715,363 A | 12/1987 | Detty |
| 4,723,539 A | 2/1988 | Townsend |
| 4,753,240 A | 6/1988 | Sparks |
| D298,568 S | 11/1988 | Womack et al. |
| 4,791,916 A | 12/1988 | Paez |
| 4,803,975 A | 2/1989 | Meyers |
| 4,854,308 A | 8/1989 | Drillio |
| 4,856,501 A | 8/1989 | Castillo et al. |
| 4,886,054 A | 12/1989 | Castillo et al. |
| 4,938,207 A | 7/1990 | Vargo |
| 4,940,044 A | 7/1990 | Castillo |
| 4,964,402 A | 10/1990 | Grim et al. |
| 4,986,264 A | 1/1991 | Miller |
| D318,736 S | 7/1991 | Castillo |
| 5,063,916 A | 11/1991 | France et al. |
| 5,121,742 A | 6/1992 | Engen |
| 5,135,469 A | 8/1992 | Castillo |
| 5,230,697 A | 7/1993 | Castillo et al. |
| 5,288,287 A | 2/1994 | Castillo et al. |
| D346,028 S | 4/1994 | Lengyel |
| 5,398,383 A * | 3/1995 | Bingold .................... 24/16 PB |
| D357,070 S * | 4/1995 | Castillo ..................... D24/190 |
| 5,743,117 A * | 4/1998 | Woo et al. ..................... 70/16 |
| 5,947,916 A * | 9/1999 | Riedlinger ..................... 602/5 |
| 6,210,352 B1 * | 4/2001 | Williams et al. ............... 602/3 |
| 6,464,657 B1 * | 10/2002 | Castillo ....................... 602/26 |

* cited by examiner

JOINT BRACE WITH LIMB-CONFORMING ARCUATELY ADJUSTABLE CUFFS

CROSS REFERENCE TO RELATED APPLICATIONS

This application is a continuation-in-part of U.S. patent application Ser. No. 09/578,125, filed May 24, 2000 now U.S. Pat. No. 6,464,657.

STATEMENT RE: FEDERALLY SPONSORED RESEARCH/DEVELOPMENT

Not Applicable

BACKGROUND OF THE INVENTION

This invention relates in general to anatomical support braces, and in particular to an exteriorly positionable anatomical brace having tensionably tightenable cuffs situated about respective limb structures on either side of a uniting pivoting joint such as a knee joint to thereby provide adjustable limb-conforming arcuate tightening pressure about the respective limb structures and resulting stability to the supported joint.

Both injury and disease can affect the health, well-being, and operability of various joints of the human body. Chief among such joints are the knee and elbow where disease such as osteo-arthritis can curtail normal activity or where an injury such as a sports-related abuse or impact can prevent or severely limit continued activity. One manner of treating such joint conditions and/or preventing or reducing the severity of sports related injuries is to fit the wearer with an appropriate brace whereby a pivotal support member is positioned adjacent the affected joint and held in place usually by cuffs situated around limb structure sites above and below the supported joint. As is apparent, the cuffs are responsible for stabilizing the support member and therefore must be well secured to their associated limbs. To accomplish such securement, previous designs offered either soft cuffs which afforded no stability, or rigid custom-made cuffs, which are non-adjustable. Further, present cuffs are typically provided with one or more straps that are tightened around each limb structure and retained by buckles, hook-and-loop connections, or the like while the cuff itself generally is substantially permanently preformed to a particular arcuate radius. As is evident, however, such present-day construction is generally deficient in that cuff tightening, and therefore brace stabilization, is limited by the strength of the user in manipulating the straps, buckles, etc., as well as in the flexibility and tensionability of the cuff structure itself. In view of these limitations, it is apparent that a need is present for an exteriorly positionable anatomical brace wherein the tightness of cuffs can be adjusted for effective brace engagement. Accordingly, the primary object of the present invention is to provide an anatomical brace where limb-structure embracing cuffs thereof are arcuately adjustable for tightenable configuration to adjacent limb structures.

Another object of the present invention is to provide an anatomical brace where arcuate adjustment configurations of the cuffs are maintained upon brace removal.

Yet another object of the present invention is to provide an anatomical brace where cuff adjustment of arcuate configurations can be accomplished after brace placement on the involved limb.

These and other objects of the present invention will become apparent throughout the description thereof which now follows.

BRIEF SUMMARY OF THE INVENTION

The present invention is an exteriorly positionable anatomical brace for stabilizing a uniting pivoting joint such as a knee joint disposed between a first and second limb structure of a living being. The brace comprises an upper frame member and a lower frame member joined together by a pivoting joint member, with each such frame member having secured thereon a respective cuff for encompassing a portion of each limb structure above and below the joint. Retention of the brace in place at the joint site is preferably accomplished with respective upper and lower securement members each wrapping around a respective limb structure in alignment with and not encompassed by the cuff. Each cuff is an arcuate, tensionable, flexibly-bendable wall structure, which non-limitedly can be constructed of a polymer plastic material, having integral therewith at least one elongate tensioner in arcuately related juxtaposition with the cuff such that shortening the tensioner (like tendons in the hand, causes a bending of the tensioner which also bends the cuff. The tensioner includes an exteriorly accessible adjuster for incrementally drawing the lateral end of the tensioner medially for arcuately tightening the cuff or, oppositely, for incrementally releasing the lateral end and arcuately loosening the cuff. Once set, the adjuster maintains the chosen arcuate configuration when the brace is removed, thereby assuring a proper fit without repeated adjustment each time the brace is donned. Such cuff adjustability coupled with respective securement members respectively retains each cuff in place to provide superior and maximized anchored brace stability. In addition, thereafter the cuff may be easily re-adjusted for comfort and/or change in anatomic size.

BRIEF DESCRIPTION OF THE DRAWINGS

An illustrative and presently preferred embodiment of the invention is shown in the accompanying drawings in which:

FIG. 7c is a top plan view along line 7c–7c of FIG. 7a;

FIG. 11 is an exploded perspective view of the joint assembly of FIG. 10a.

DETAILED DESCRIPTION OF THE INVENTION

Referring first to FIGS. 1–5, a knee brace 10 is shown (FIG. 1) in place on a leg 12 of a human being. The brace 10 has an upper frame member 14 and a lower frame member 16, with each such frame member 14, 16 having secured thereon a respective cuff 18, 20 for disposition about the limb structures above and below the knee joint 22. Each cuff 18, 20 is an arcuate wall structure, which non-limitedly can be fabricated of a polymer plastic, for juxtapositioning with the respective limb structures as shown. Snap-in protective patella cups 24 can be included as shown for specific impact absorption that may occur at the patella of the knee joint 22.

The knee brace 10 is retained in place on the leg 12 with respective upper and lower securement members 26, 28 each respectively wrapping around an adjacent rear portion of the leg 12. While FIGS. 2–5 show only the upper securement member 26, it is to be understood that the following description thereof applies equally to the lower securement member 28. Thus, the securement member 26 includes a medial piece 30 and a lateral piece 32 each attached at outside edges 36, 38 thereof to an elastomeric central piece 34 disposed behind the medial and lateral pieces 30, 32. Respective inside edges 40, 42 of the medial and lateral pieces 30, 32 are provided with eyelets 44 through which is intertwined a length of non-elastomeric lace 46 in substantially the same manner as a shoe is laced to thereby permit the drawing of each inside edge 40, 42 toward each other. As would be recognized by the skilled artisan, hook-and-loop connectors (e.g. VELCRO) or other appropriate engagers can be employed in place of the length of lace 46. Finally, the elastomeric central piece 34 is secured along a generally central vertical length 48 thereof to a liner section 50 to thereby permit elasticized movement of the medial and lateral pieces 30, 32.

Figure 3:
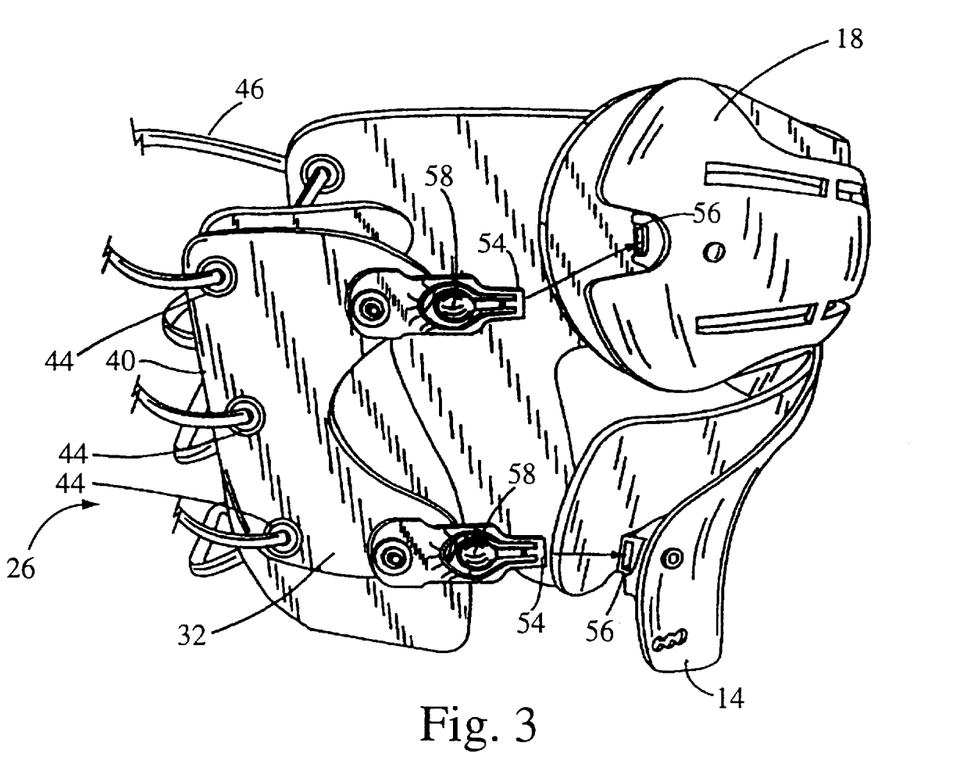
FIG. 3 is a lateral perspective view of the upper cuff and upper frame member only of FIG. 1 in disassociated relationship illustrating the end of the cuff and the securement system of the present invention.
Figure 4:
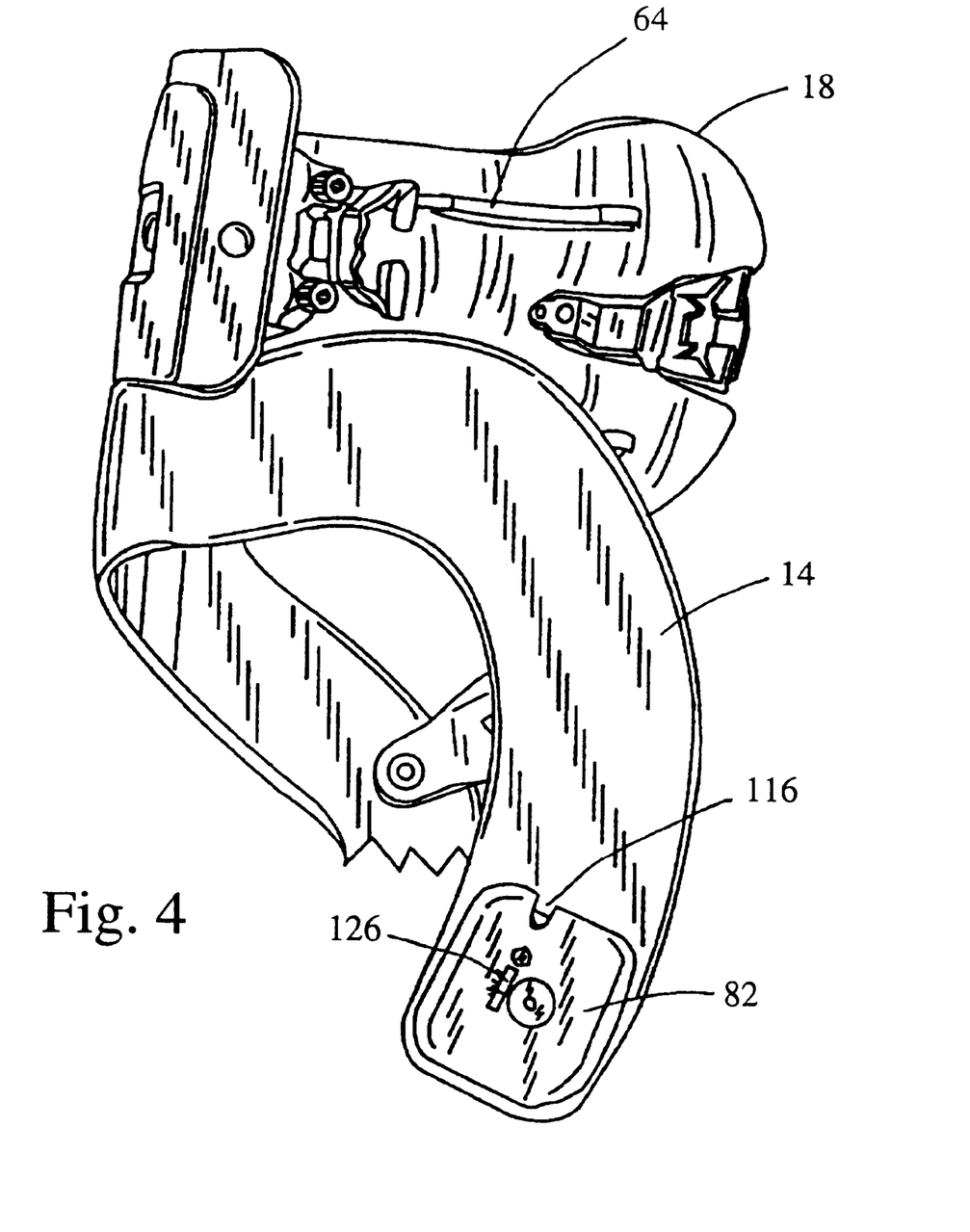
FIG. 4 is a medial perspective view of the upper cuff and upper frame member.
Figure 5:
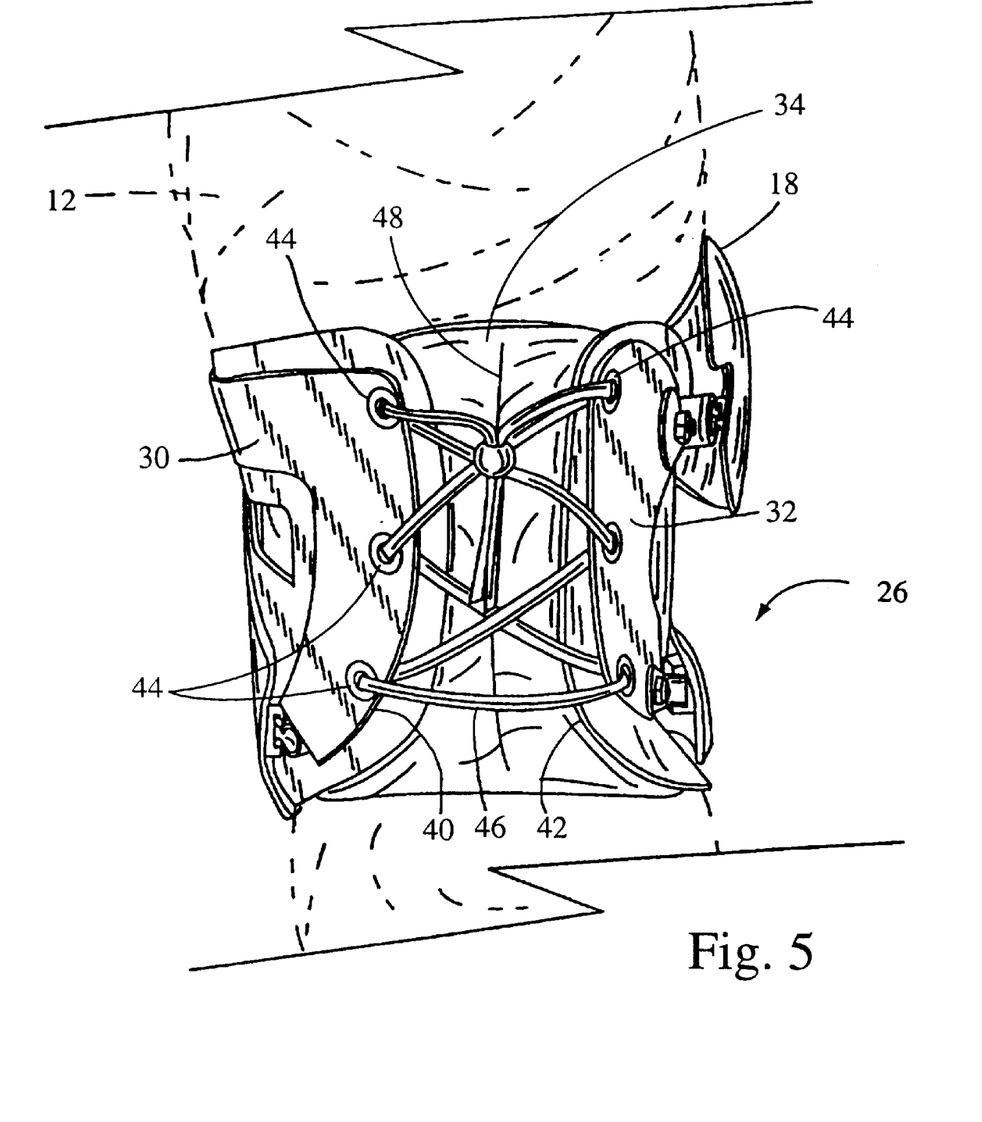
FIG. 5 is a rear perspective view of the upper cuff and upper frame member of FIG. 1 in place on a leg and illustrating the securement system of the present invention.

As illustrated in particular in FIGS. 3 and 4, the lateral piece 32 (FIG. 3) is releasably secured respectively to the upper cuff 18 and the upper frame member 14, and the medial piece 30 (FIG. 4) is releasably secured to the upper frame member 14 and the medial condyle 52, all by way of respective quick-release tab members 54 situated within respective slots 56. As shown, each tab member 54 is provided with a finger-receiving pressure button 58 which, when depressed, permits removal of the tab member 54 from the slot 56. In operation, the brace 10 is placed at the limb site of a user and positioned about the involved limb structures. Upon first placement of the brace 10, the lace 46 is tightened to appropriate tightness while the central piece 34 increases surface area on the leg 12 to disperse pressure and prevent pull from the leg 12 such that the cuff 18 is properly maintained in place. Once such lacing is accomplished the first time, re-lacing although permissible, is not required during subsequent brace use. Specifically, when a user wishes to remove the brace, the user simply presses inwardly on the pressure buttons 58 of only laterally, or, preferably, only medially, situated tab members 54 to release these tab members 54 from their respective slots 56 and remove the brace 10 from the leg 12. It is important to note that the above-described tab-member release does not require increased tension on the leg and therefore is both safe and comfortable. Subsequent re-positioning of the brace 10 merely requires placement thereof as previously situated and re-connection of the earlier disengaged tab members 54 into respective slots 56. This re-connection requires no contact with, or re-adjustment of, the lace 46 or the central piece 34, and thereby assures proper brace placement without awkward, and very possibly incorrect, orientation of the brace 10. Because the medial connection involves connection to the medial condyle 52 which is, of course, at the hinge point of the upper and lower frame members 14, 16, a closer positioning of the securement member 26 to the body joint is permitted, thereby improving joint support. While the lateral condyle 60 in the embodiment here shown does not bear a connector member, it is to be understood that such construction could be provided if desired.

Figure 1:
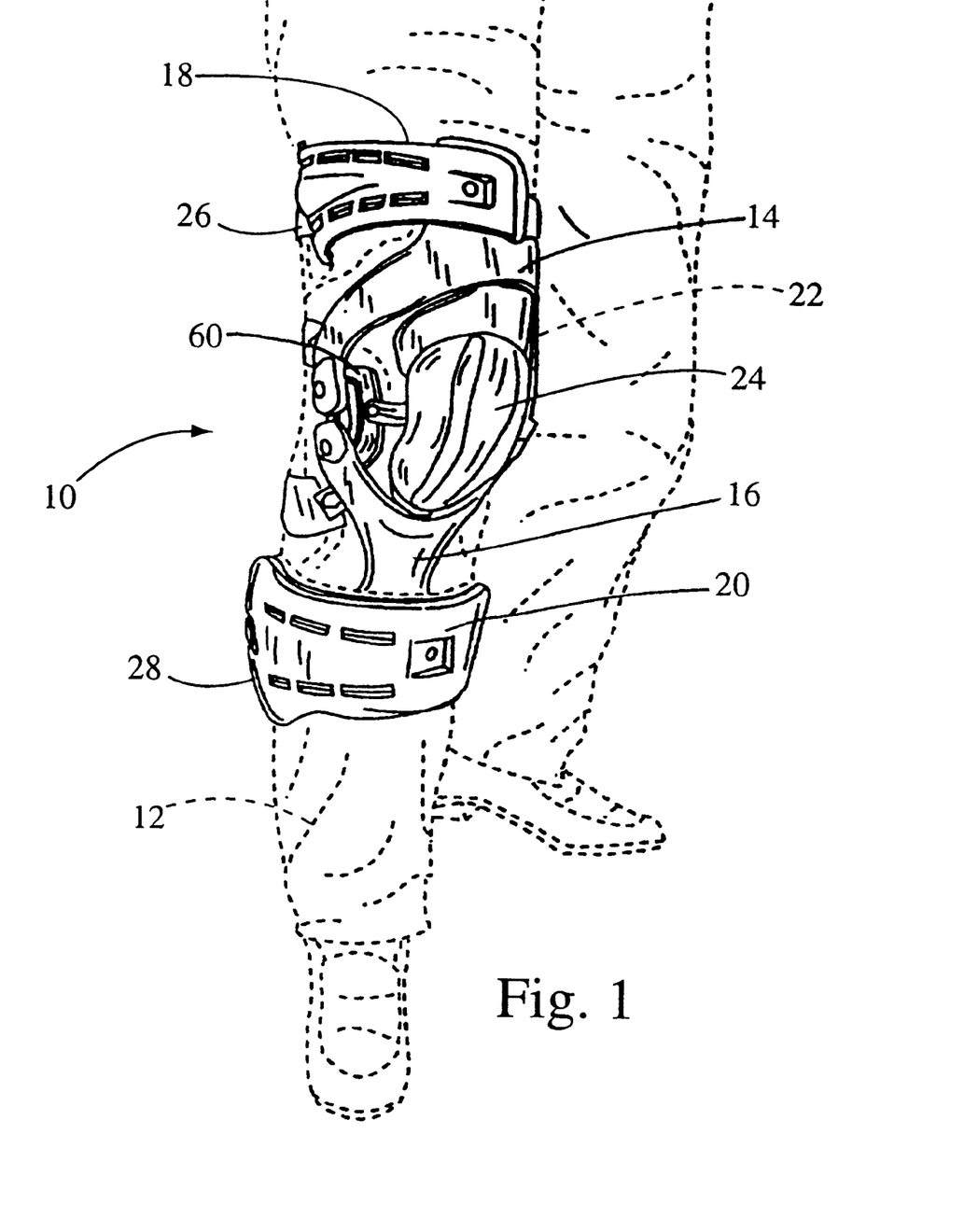
FIG. 1 is a perspective lateral view of a knee brace with upper and lower cuffs of respective upper and lower frame members in place on a user's leg shown in phantom.
Figure 2:
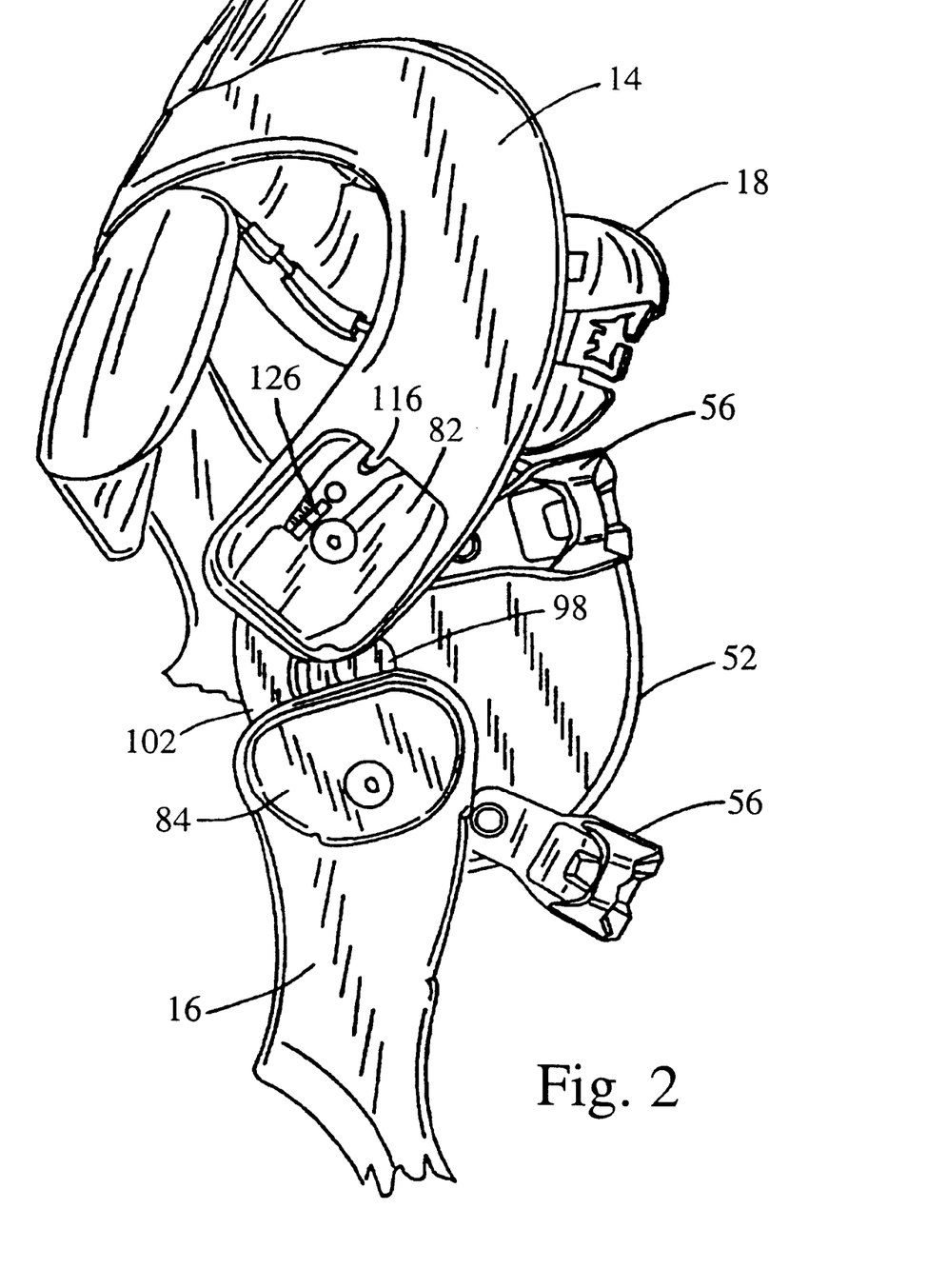
FIG. 2 is a perspective medial view of the knee brace of FIG. 1 in place on the leg.
Figure 6:
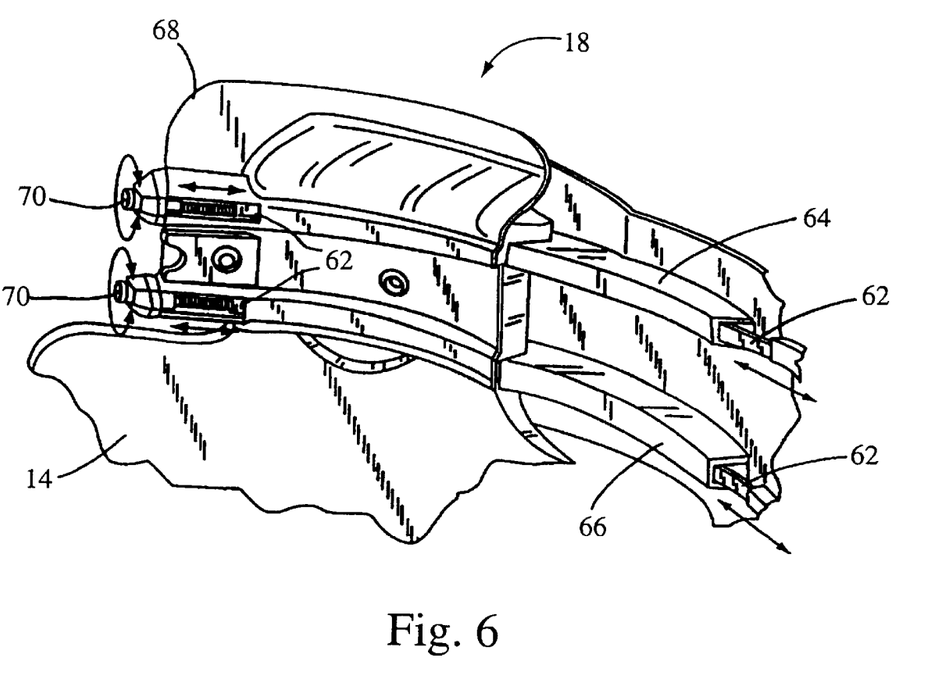
FIG. 6 is an interior perspective view of a portion of the upper cuff of FIG. 1.
Figure 7A:
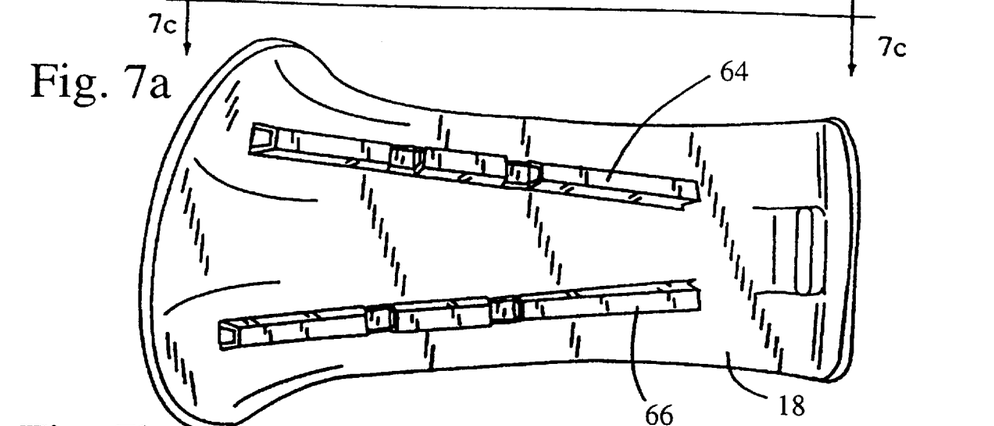
FIG. 7a is an interior side elevation view of the upper cuff of FIG. 4.
Figure 7B:
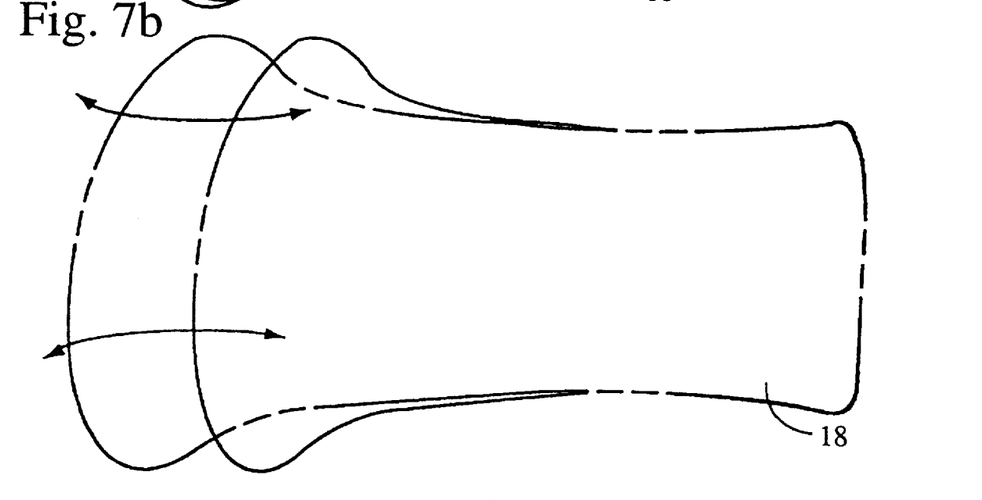
FIG. 7b is a schematic interior side elevation view of the cuff of FIG. 7a showing tensioning thereof.
Figure 7C:
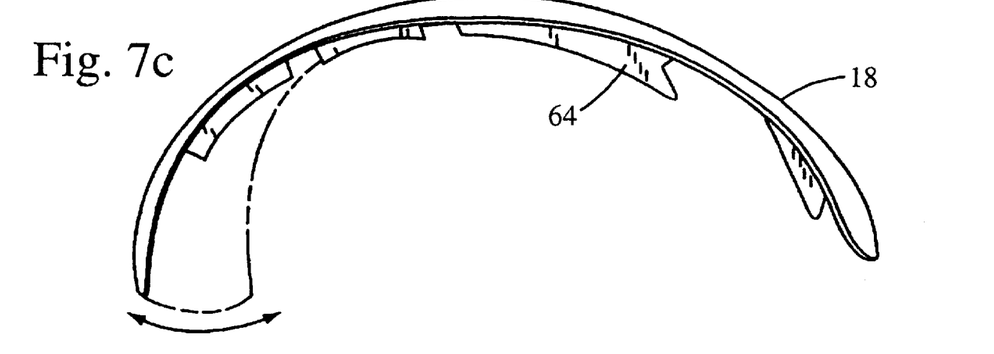
Figure 8:
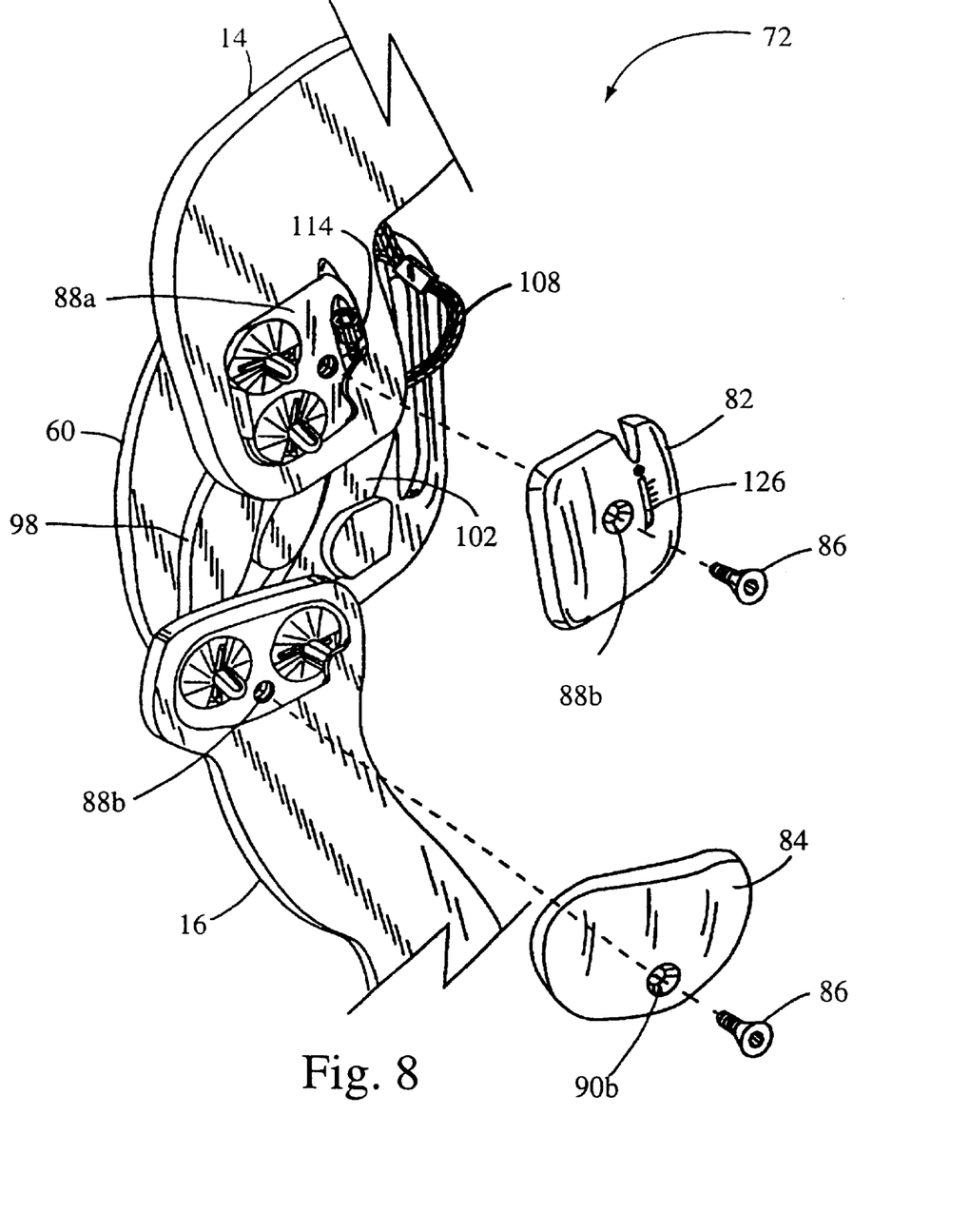
FIG. 8 is an inner perspective view of the joint assembly and respective portions of joined upper and lower frame members of FIG. 1.
Figure 9:
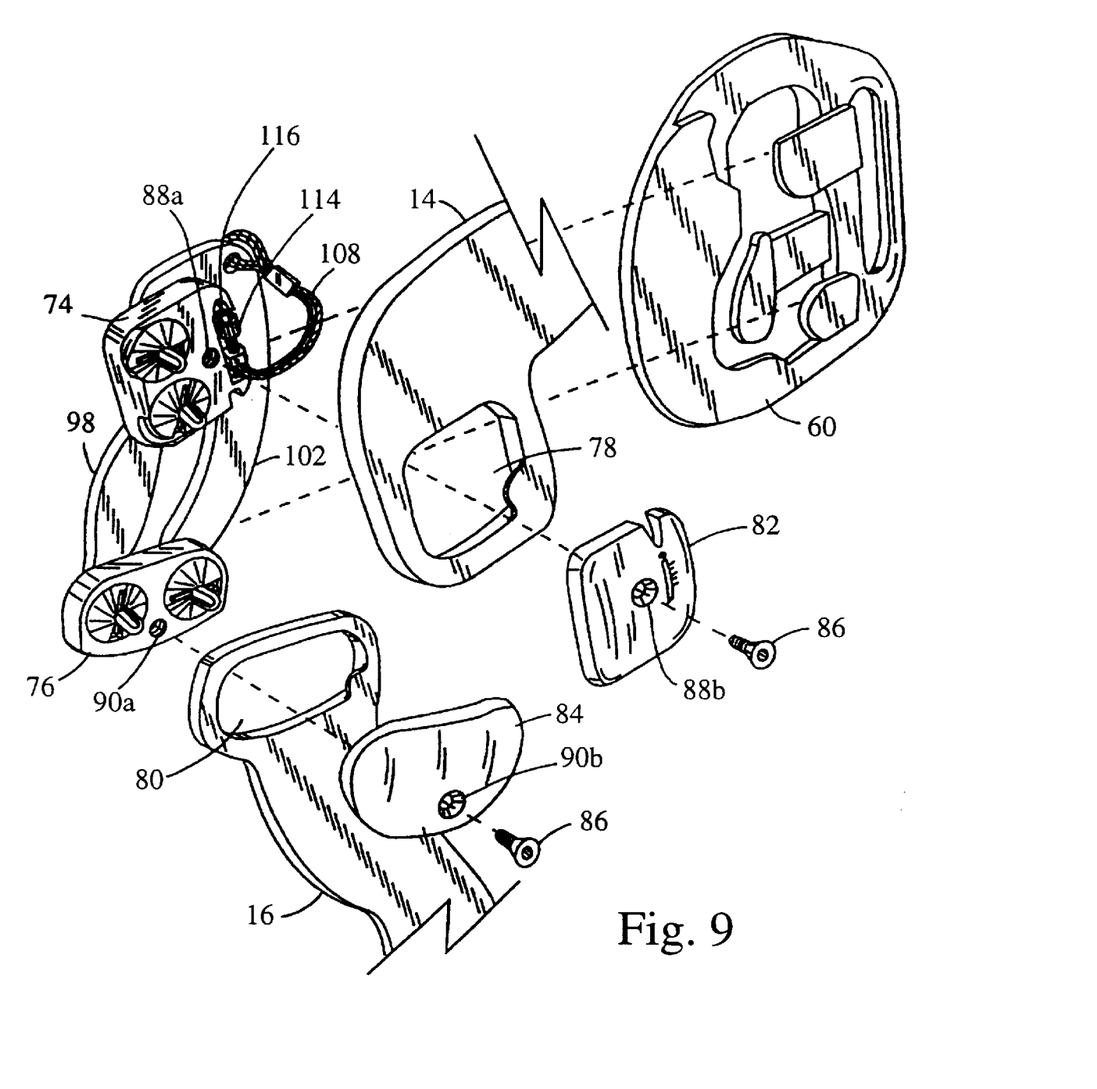
FIG. 9 is an exploded perspective view of the joint assembly and frame members of FIG. 8.
Figures 10A, 10B:
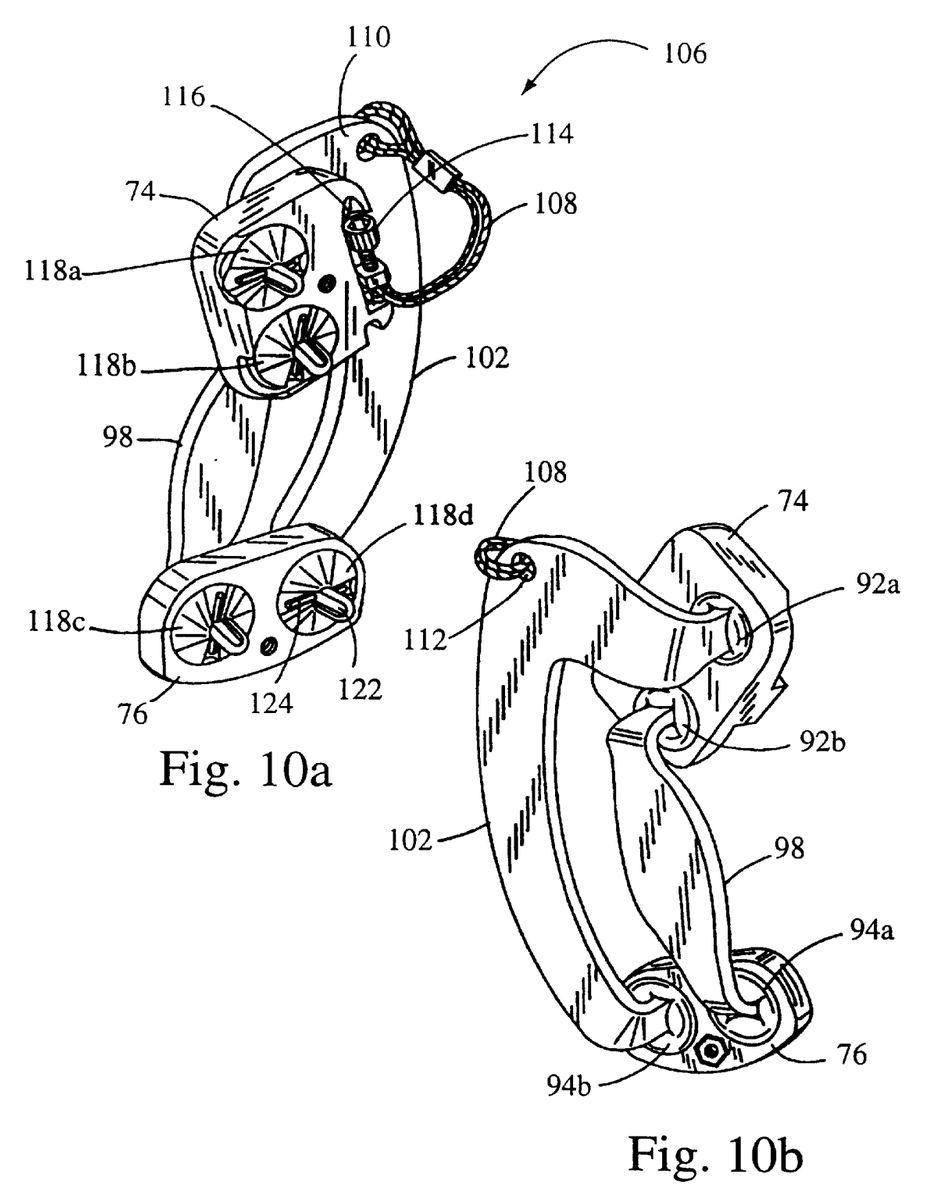
FIGS. 10a and 10b are perspective views of the inner and outer sides of the joint assembly of FIG. 8.
Figure 11:
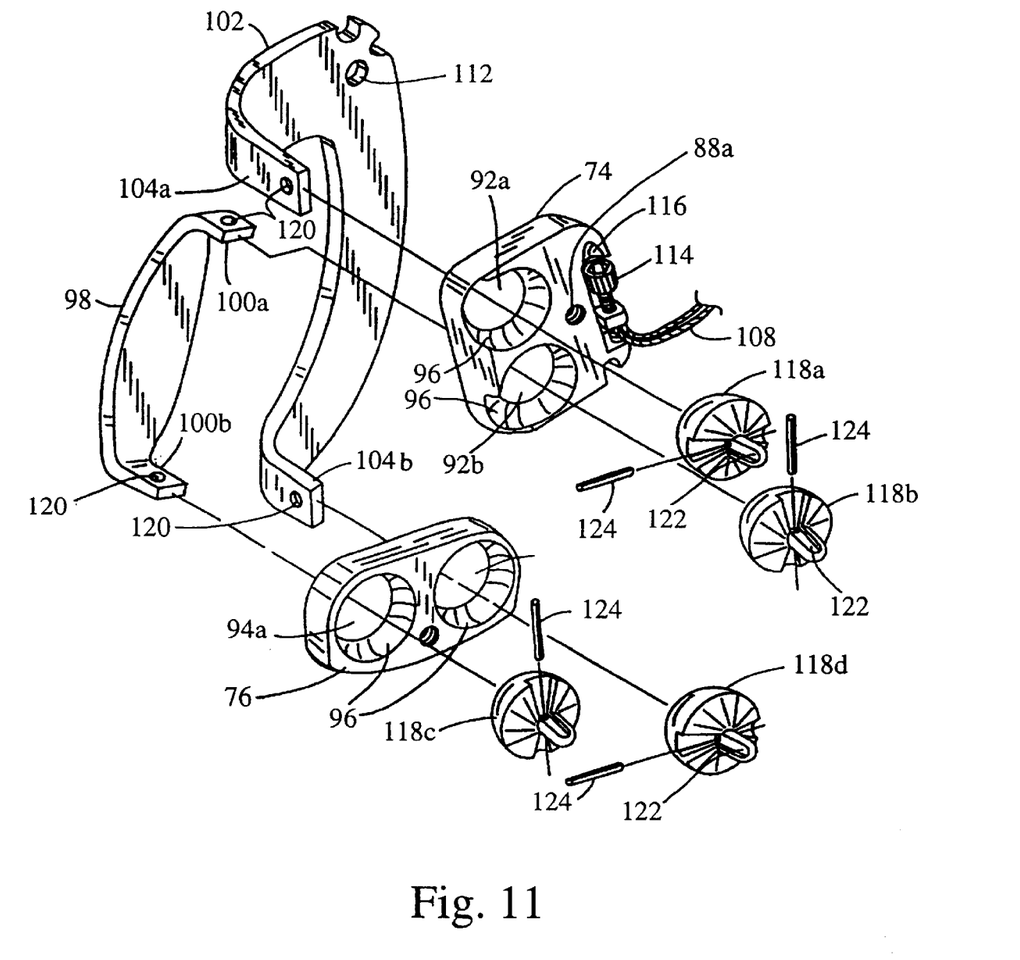

Construction of the cuffs 18, 20 is illustrated in FIGS. 6–7c. Both the upper cuff 18 and lower cuff 20 are substantially identical in construction except for overall size since, of course, the lower cuff 20 encompasses a smaller-diameter limb portion below the knee joint 22. As shown particularly in FIGS. 6 and 7a with respect to the upper cuff 18, whose following description also applies to the lower cuff 20, the cuff 18 has two tensioning strip members 62, integral therewith and disposed within respective non-continuous sleeves 64, 66 that are structurally a part of the cuff 18. Each cuff defines a longitudinal axis 65, and each sleeve 64, 66 has a lateral end 67 and a medial end 69, as shown in FIG. 7a. The sleeves 64, 66 of each cuff 18 converge toward each other from the lateral end 67 toward the medial end 69 of the sleeves 64, 66. Each strip member 62, which preferably is fabricated of titanium, stainless steel, or similar material possessing similar tensioning properties, continues medially into a cuff mount 68 that functions to secure the cuff 18 to the upper frame member 14. Finally, a respective exteriorly-accessible threaded screw 70 extends into each strip member 62 for adjusting tension in each strip member 62 and simultaneously adjusting the arc defined by the upper cuff 18. Thus, clockwise turning of the screw 70 incrementally draws the lateral end of the strip member 62 medially for arcuately tightening the cuff 18, while counter clockwise turning of the screw 70 incrementally releases the lateral end of the strip member 62 for arcuately loosening the cuff 18. Operationally, the brace 10 is fitted to a user by encompassing the cuffs about the respective limb structures above and below the knee joint 22 as seen in FIG. 1. Once the upper cuff 18 is situated about the limb structure, the screws 70 are threadingly advanced to thereby cause movement of the lateral end of the cuff 18, as illustrated in FIGS. 7b and 7c, against the limb structure as the strip members 62 are forced to bend toward the encompassed limb structure. Continued screw advancement increases tightening of the cuff 18 against the encompassed limb structure to thereby accomplish superior anchoring and fit of the brace 10 and consequent stabilization of the knee joint 22. As earlier noted, the lower cuff 20 is constructed in the same manner as the upper cuff 18 and therefore encompasses and embraces the limb structure below the knee joint 22 in like fashion. Although preferably the strip members 62 are fabricated as shown, those skilled in the art will recognize that they can additionally be fabricated as cables or other elongate elements.

Referring to FIGS. 8–11, the pivoting assembly 72 uniting the upper and lower frame members 14, 16 is illustrated. The assembly 72 includes an upper housing 74 and a lower housing 76 that fit, respectively, into a complementarity shaped opening 78 of the upper frame member 14 and a complementarity shaped opening 80 of the lower frame member 16. However, it is contemplated that the housing 74 and 76 could be integrally formed with the frame members. Once so positioned, respective caps 82, 84 are held in place with conventional set screws 86 passing respectively through apertures 88a, 88b and 90a, 90b. The lateral condyle 60 resides between the assembly 72 and the knee joint 22. Both the upper and lower housings 74, 76 have two respective openings 92a, 92b and 94a, 94b each having respective sidewalls 96 shaped to nest a spherical shape. Disposed between two openings 92b, 94a of the housings 74, 76 is a forward arm member 98 having generally perpendicularly angled first and second ends 100a, 100b directable toward the openings 92b, 94a. In like manner, a rearward arm member 102 having generally perpendicularly angled first and second ends 104a, 104b is disposed between two openings 92a, 94b of the housings 74, 76 such that the ends 104a, 104b are directable toward the openings 92a, 94b. A cable assembly 106 includes a cable 108 extending from the upper housing 74 to an upper edge portion 110 through an aperture 112 of the rearward arm member 102, and is provided with a conventional set screw 114 at one end thereof for extending or shortening the length of the cable 108 disposed between the rearward arm member 102 and upper housing 74. Such length adjustment is accomplished with an Allen wrench inserted into the enterable channel 116 leading to the set screw 114. Because the upper housing 74 resides within the upper frame member 14, the cable 108 functions as a joint extension limiter to determine the travel distance of the upper frame member 14 from the joint and thus the pivotal distance of the upper and lower frame members 14, 16 in relation to each other. An opening 126 can be provided in the cap 82 such that the progressive placement of the cable 108 can be observed exteriorly and such placement can be made identical for both the lateral and medial sides. Two additional benefits are provided by the cable 108 in that, first, infinite pivot-distance adjustability, as opposed to prior-art pre-sized stop members, allows great flexibility in leg extension, and, second, the cable itself has a dampening, or minimal stretch, effect that results in a softer extension stop and a consequent reduced risk of joint trauma.

As earlier described, the sidewalls 96 of the openings 92a, 92b and 94a, 94b are shaped to nest spherical forms. As clearly illustrated in FIG. 11, spherical sockets 118a, 118b, 118c, 118d are disposed in these openings 92a, 92b and 94a, 94b in the constructed assembly 72, and each such socket accepts one respective perpendicularly angled end of forward and rearward arm members 98, 102. Each angled end 100a, 100b, 104a, 104b has an aperture 120 there through which mates with a transverse aperture 122 of each socket 118a, 118b, 118c, 118d such that respective pins 124 can pass through such mated apertures and retain the angled ends 100a, 100b, 104a, 104b within the sockets 118a, 118b, 118c, 118d. Because of the spherical interface between each socket 118a, 118b, 118c, 118d and each sidewall 96, multi planar movement of the upper and lower frame members 14, 16 in relation to each other can be accomplished. In particular, the different pivot points thus provided allow different pivot ratios as needed for both lateral and medial sides to thereby simulate actual knee joint movement. This is, of course, in contrast to parallel planar hinges as found in the prior art where the knee joint and limb structures of a user are forced to adapt to knee brace construction instead of the knee brace adapting to the needs of the user. The present knee brace 10, because of the multi planar and potentially differing pivot ratios and consequent multi planar movement capabilities of the lower frame member 16 in relation to the upper frame member 14, provides automatic tibia alignment and automatic anatomical changes over time by accommodating anatomical differences among users. These properties accomplish all-important positive three-point positioning at the quadriceps muscle, the gastrocnemius (calf) muscle, and the knee joint itself. In this manner, stabilization and support of a uniting pivoting joint occurs economically, through an "off-the-shelf" brace, and, simultaneously, most effectively through continual self-alignment capabilities combined with sound limb-structure stability.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. An exteriorly positionable anatomical brace for stabilizing a uniting pivoting joint disposed between a first and second limb structure of a living being, the brace comprising:
 a) an upper frame member and a lower frame member;
 b) a pivoting joint member connecting the upper and lower frame members;
 c) an upper cuff for encompassing a portion of the first limb structure and secured to the upper frame member with a cuff mount, and a lower cuff for encompassing a portion of the second limb structure and secured to the lower frame member with a cuff mount, each cuff comprising:
  i) an arcuate, tensionable, flexibly-bendable wall structure;
  ii) at least one elongate tensioner in arcuately related juxtaposition with the cuff, whereby bending the tensioner also bends the cuff, the tensioner having a lateral end and a medial end;
  iii) an exteriorly accessible adjuster for incrementally drawing the lateral end of the tensioner medially to arcuately tighten the cuff and for incrementally releasing the lateral end to arcuately loosen the cuff; and
  iv) two sleeves structurally a part of each cuff, with each sleeve having a lateral end and a medial end and wherein the sleeves converge toward each other from the lateral ends toward the medial ends of the sleeves, and further wherein each sleeve houses one elongate tensioner; and
 d) an upper securement member for securing the upper cuff to the first limb structure, and a lower securement member for securing the lower cuff to the second limb structure.

2. An exteriorly positionable anatomical brace as claimed in claim 1 wherein each elongate tensioner is configured as a strip member.

3. An exteriorly positionable anatomical brace as claimed in claim 2 wherein each strip member continues medially into the respective cuff mount such that the medial end of the strip member is accessible.

4. An exteriorly positionable anatomical brace as claimed in claim 3 wherein the adjuster comprises a threaded screw extending into the medial end of the strip member, whereby rotation of the screw in a first direction incrementally draws the lateral end of the strip member medially for arcuately tightening the cuff and rotation of the screw in a second direction incrementally releases the lateral end of the strip member for arcuately loosening the cuff.

5. A cuff for an anatomical brace for stabilizing a uniting pivoting joint disposed between a first and second limb structure of a living being, the cuff comprising:
 a) an arcuate, tensionable, flexibly-bendable wall structure;

b) at least one elongate tensioner in arcuately related juxtaposition with the cuff, whereby bending the tensioner also bends the cuff, the tensioner having a lateral end and a medial end, each tensioner being configured as a strip member wherein the medial end of the strip member is exteriorly accessible;

c) an exteriorly accessible adjuster for incrementally drawing the lateral end of the tensioner medially to arcuately tighten the cuff and for incrementally releasing the lateral end to arcuately loosen the cuff wherein the adjuster comprises a threaded screw extending into the medial end of the strip member, whereby rotation of the screw in a first direction incrementally draws the lateral end of the strip member medially for arcuately tightening the cuff, and rotation of the screw in a second direction incrementally releases the lateral end of the strip member for arcuately loosening the cuff; and d) two sleeves structurally a part of the cuff, with each sleeve having a lateral end and a medial end and wherein the sleeves converge toward each other from the lateral ends toward the medial ends of the sleeves, and further wherein each sleeve houses one elongate tensioner.

6. A cuff for anchoring and fitting an anatomical brace about a limb structure of a living being, the cuff comprising:

a) an arcuate, tensionable, flexibly-bendable wall structure defining a longitudinal axis transverse to a longitudinal axis of the limb structure;

b) at least one elongate tensioner retained within the wall structure and in arcuately related juxtaposition with the wall structure along the longitudinal axis of the wall structure, whereby bending the tensioner also bends the cuff, the tensioner having a lateral end and a medial end; and c) an exteriorly accessible adjuster for incrementally drawing the lateral end of the tensioner medially to arcuately tighten the cuff and for incrementally releasing the lateral end to arcuately loosen the cuff.

7. A cuff as claimed in claim 6 additionally comprising two sleeves structurally a part of the wall structure, with each sleeve having a lateral end and a medial end and wherein the sleeves converge toward each other medially, and further wherein each sleeve houses one elongate tensioner.

8. A cuff as claimed in claim 7 wherein each elongate tensioner is configured as a strip member.

9. A cuff as claimed in claim 8 wherein the medial end of the strip member is exteriorly accessible.

10. An exteriorly positionable anatomical brace for stabilizing a uniting pivoting joint disposed between a first limb structure and a second limb structure of a living being, the brace comprising:

a) an upper cuff partially encompassable about the first limb structure and a lower cuff partially encompassable about the second limb structure, each cuff defining a longitudinal axis transverse in relation to a longitudinal axis of the respective limb structure, each cuff having at least one sleeve wherein each sleeve extends along the longitudinal axis of the cuff; and b) at least one elongate tensioner integral with each cuff, wherein at least a portion of each of the at least one elongate tensioner is retained within the respective at least one sleeve.

11. An exteriorly positionable anatomical brace for stabilizing a uniting pivoting joint of a living being, the brace comprising:

a) an upper frame member and a lower frame member, each frame member having two generally spherical sockets;

b) a pivoting joint member connecting the upper and lower frame members, the pivoting joint member comprising two opposing assemblies each sized and configured to be on one lateral side of the united pivoting joint, with each assembly comprising:

i) a forward arm member having a generally spherical first end and a generally spherical second end, and a rearward arm member in tandem relationship with the forward arm member and having a generally spherical first end and a generally spherical second end;

ii) wherein the spherical first ends of the forward and rearward arm members are sized and configured so as to be received by the two generally spherical sockets of the upper frame member, and the spherical second ends of the forward and rearward members are sized and configured so as to be received by the two generally spherical sockets of the lower frame member for multiplanar movement between upper and lower frame members.

* * * * *